United States Patent [19]

Wilson

[11] 4,300,575
[45] Nov. 17, 1981

[54] AIR-PERMEABLE DISPOSABLE ELECTRODE

[75] Inventor: Michael A. Wilson, Loveland, Colo.

[73] Assignee: Staodynamics, Inc., Longmont, Colo.

[21] Appl. No.: 51,593

[22] Filed: Jun. 25, 1979

[51] Int. Cl.³ .............................................. A61N 1/04
[52] U.S. Cl. ..................... 128/798; 128/802
[58] Field of Search ............................. 128/639–641, 128/644, 303.13, 783, 798, 802, 803

[56] References Cited

U.S. PATENT DOCUMENTS

| | | | |
|---|---|---|---|
| 3,788,317 | 1/1974 | McCormick | 128/641 |
| 3,911,906 | 10/1975 | Reinhold, Jr. | 128/641 |
| 3,976,055 | 8/1976 | Monter et al. | 128/641 X |
| 3,993,049 | 11/1976 | Kater | 128/641 X |
| 3,998,215 | 12/1976 | Anderson et al. | 128/641 |
| 4,008,721 | 2/1977 | Burton | 128/802 |
| 4,066,078 | 1/1978 | Berg | 128/641 |
| 4,125,110 | 11/1978 | Hymes | 128/641 |
| 4,141,366 | 2/1979 | Cross, Jr. et al. | 128/640 |

FOREIGN PATENT DOCUMENTS

| | | | |
|---|---|---|---|
| 13888 | 4/1970 | Australia | 128/798 |
| 2814061 | 10/1978 | Fed. Rep. of Germany | 128/303.13 |
| 2727396 | 12/1978 | Fed. Rep. of Germany | 128/640 |
| 2271846 | 12/1975 | France | 128/803 |

Primary Examiner—Lee S. Cohen
Attorney, Agent, or Firm—O'Rourke & Harris

[57] ABSTRACT

A disposable electrode is disclosed that is air-permeable over at least that portion of the electrode that is engageable with the skin of a patient, and is non-metallic and nonionic. The electrode includes a conductive silicone pad adapted to receive one end of an electrical lead from an active electrical instrument, and particularly an electronic medical instrument such as a transcutaneous nerve stimulator. The pad engages a permeable conductive element that is skin engageable through a permeable conductive adhesive coating. The permeable conductive element is formed primarily from karaya and carbon black so that the element can "breathe". The permeable conductive adhesive coating is likewise formed primarily from karaya so that the coating can also "breathe". A cover, likewise of air-permeable material, is provided with an adhesive on the inner side contacting the rear portions of the pad and conductive element with the cover extending outwardly thereof so that the outer edges of the inner side of the cover are engageable with the skin of a patient to hold the electrode in position. A carrier, preferably release paper, is also provided to cover the adhesive coating on the conductive element and the outer portions of the cover to protect the electrode until use on a patient.

15 Claims, 8 Drawing Figures

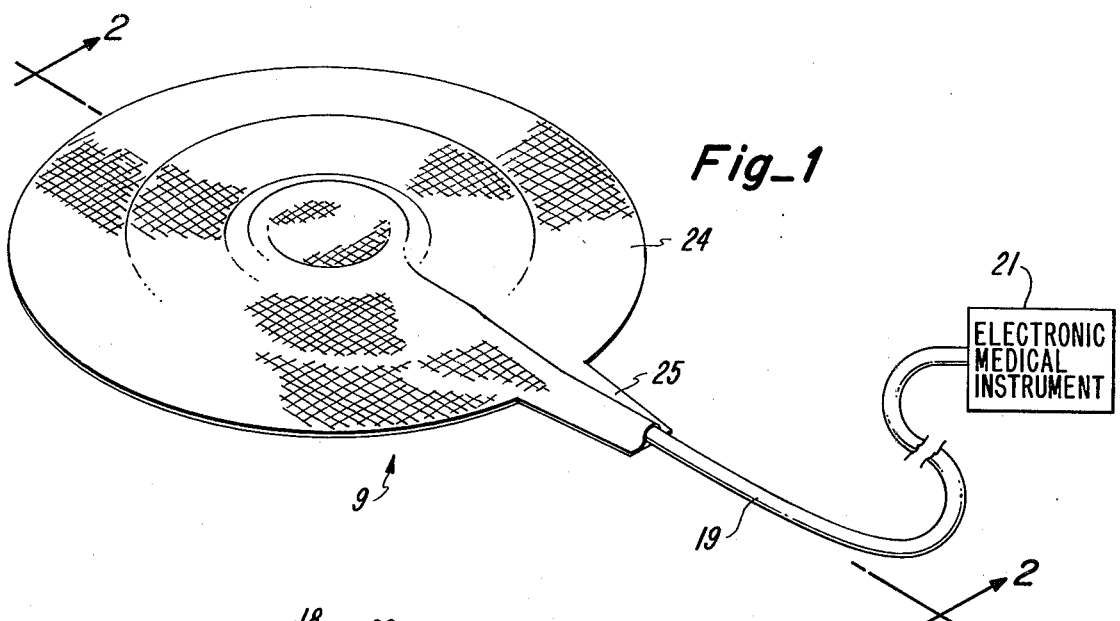
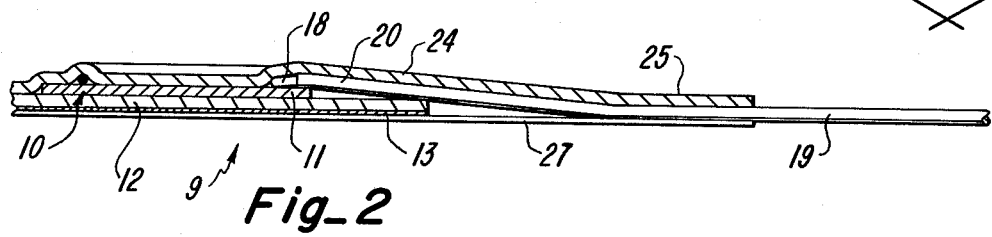
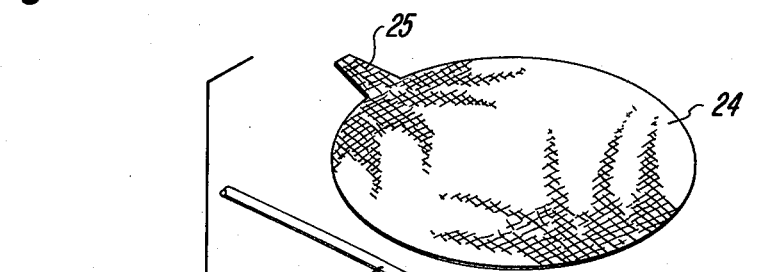
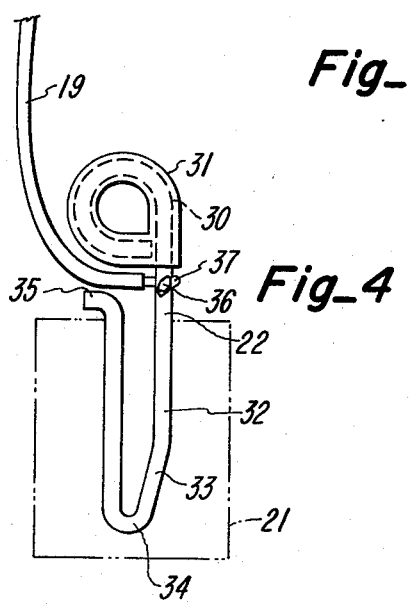
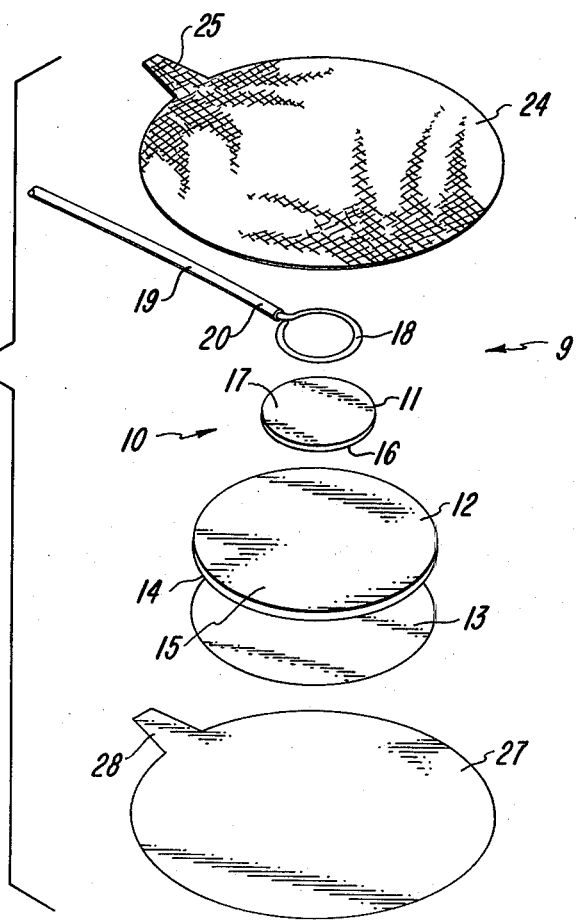

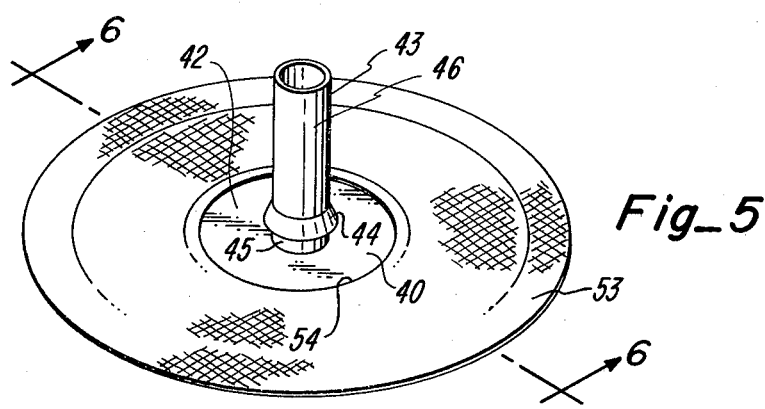
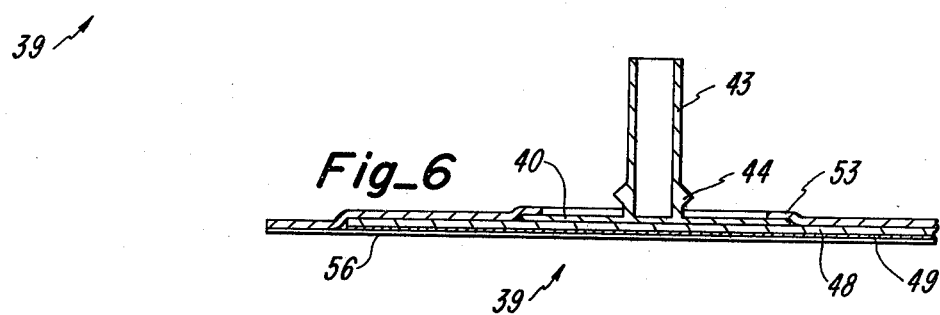
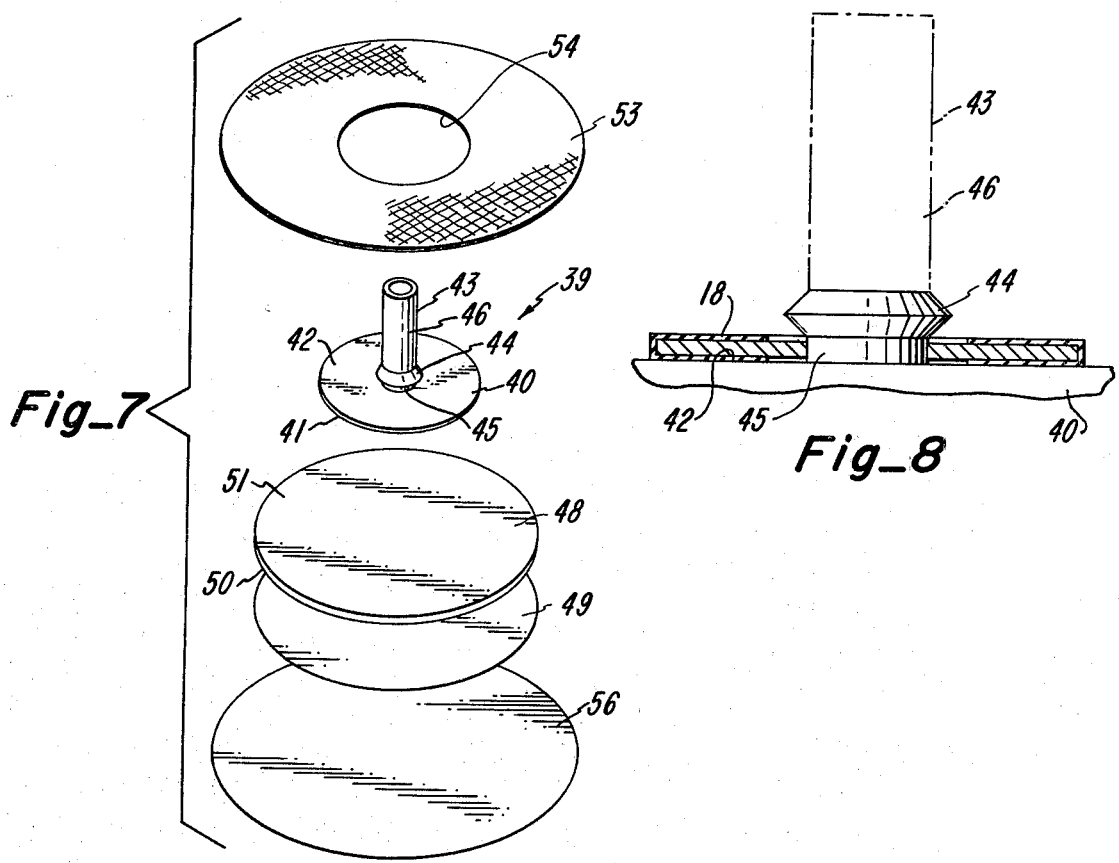

AIR-PERMEABLE DISPOSABLE ELECTRODE

RELATED INVENTION

This invention is related to my co-pending U.S. patent application Ser. No. 956,770, filed Nov. 28, 1978, entitled "Disposable Electrode", now abandoned.

FIELD OF THE INVENTION

This invention relates to a disposable electrode and, more particularly, relates to a skin engageable, air-permeable, disposable electrode that is particularly useful with an active electronic medical instrument.

BACKGROUND OF THE INVENTION

The use of electrodes is well known in connection with medical instruments such as electronic medical instruments. One such instrument, for example, is a transcutaneous nerve stimulator, such as shown in U.S. Pat. No. 4,014,347. Such electronic medical instruments are active instruments and commonly utilize electrodes which are positioned so as to be engageable with, but do not penetrate, the skin of the patient to be treated, with the electrodes being driven by the instrument (i.e., the instrument provides electrical current to the electrodes and hence the electrodes are active as opposed to merely sensing a body characteristic).

While skin engageable electrodes have heretofore been suggested and/or utilized, and while such electrodes have been heretofore utilized with active devices, such electrodes have not been completely satisfactory due, at least in part, to the physical properties and/or dimensions of the electrode and/or difficulties encountered in the use of such electrodes.

With respect to electrode dimensions, at least some dimensions have been too large for effective usage or, in some cases, too small so as to cause skin burns to be suffered by the patient.

With respect to electrode properties, at least some such electrodes have lacked the necessary flexibility and/or have caused complaints due to diverse problems such as might be presented by allergies or other reactions due to adhesives and/or gels utilized.

One such problem is that due to metallic electrodes or electrodes having a substantial amount of metal adjacent to the skin, when such electrodes are used with active devices. Such electrodes can cause problems, as for example, through ionization of the metal and subsequent incorporation into the body of the patient due to current flow through the electrodes.

With respect to use of the electrodes, it has been heretofore commonly necessary to take a number of steps in order to prepare and/or place the electrodes in satisfactory skin engagement. In addition, at least in some cases, electrode use has not been fully effective due at least in part to failure to properly locate the electrodes on the skin of the patient to gain adequate conduction therethrough, which can occur, for example, if a gel is not utilized or the gel utilized is not uniform across the portion of the electrode contiguous to the skin.

In the prior art, electrodes for use with medical instruments are shown, by way of example, in U.S. Pat. Nos. 423,549; 792,066; 1,211,492; 1,889,272; 2,065,295; 3,534,727; 3,746,004; 3,817,252; 3,822,708; 3,911,930; 4,014,347; 4,026,278; 4,051,842 and 4,072,145. Of these, U.S. Pat. No. 3,746,004 is particularly directed to a disposable electrode. In addition, my U.S. patent application Ser. No. 956,770, filed Nov. 11, 1978, and entitled "Disposable Electrode" is directed to nonmetallic and nonionic electrodes for medical instruments that require a minimum of preparatory steps for usage.

With respect to electrode usage, however, it has still often been necessary to remove the electrodes after a relatively short period of time to alleviate problems due to virtual sealing of the skin covered by the electrode. Thus, electrodes, and particularly disposable electrodes, could not heretofore be utilized as effectively as might be the case where air could come into skin contact as is necessary, at least with respect to many patients, to avoid, or at least alleviate, skin problems induced by sealing of the skin against air contact.

It has also been found desirable to provide an electrical lead one end of which is either permanently adhered to the electrode or at least can easily be connected thereto in a manner such that the lead does not become easily disconnected during use by a patient. Likewise, it has also been found desirable to provide a connection at the other end of the electrode whereby a patient can easily connect the electrode to the electrical instrument and easily disconnect the same therefrom.

SUMMARY OF THE INVENTION

This invention provides an improved electrode that is disposable, skin engageable, and is particularly useful with electrical instruments such as active electronic medical instruments. The electrode has improved dimensions and properties, may be used without requiring extensive preparatory steps by the user, and is readily connected and disconnected for use. The electrode is also nonmetallic, nonionic, is of small size, is flexible, and is air-permeable so that the electrode does not provide an air barrier or seal to the skin engaged by the electrode whereby the electrode may be continuously used for relatively long periods of time.

It is therefore an object of this invention to provide an improved electrode.

It is another object of this invention to provide an improved skin engageable, disposable electrode for use with electrical instruments.

It is still another object of this invention to provide an improved disposable electrode that is particularly useful with active electronic medical instruments.

It is yet another object of this invention to provide an improved electrode that has improved dimensions and/or properties and does not require extensive preparatory steps by the user.

It is yet another object of this invention to provide an improved electrode that is air-permeable to allow air contact therethrough to the skin covered by the electrode.

It is still another object of this invention to provide an improved electrode that is of small size and is readily connected to and disconnected from an associated medical instrument.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the application of the principles thereof, and in which:

FIG. 1 is a perspective view of one embodiment of the disposable electrode of this invention;

FIG. 2 is a side-sectional view taken through lines 2—2 as shown in FIG. 1;

FIG. 3 is an exploded perspective view of the electrode of this invention as shown in FIGS. 1 and 2;

FIG. 4 is a side view of the hook connector which may be utilized for connection of the electrode to an electronic medical instrument;

FIG. 5 is a perspective view of a second embodiment of the disposable electrode of this invention;

FIG. 6 is a side-sectional view taken through lines 6—6 as shown in FIG. 5;

FIG. 7 is an exploded perspective view of the electrode of this invention as shown in FIGS. 5 and 6, and FIG. 8 is a side view similar to FIG. 6 except indicating connection of an electrical lead to the electrode.

DESCRIPTION OF THE INVENTION

Electrode 9 is shown in FIGS. 1 through 3. Electrode 9 has a conductive portion 10 that includes a conductive silicone pad 11 and a conductive element 12 with a conductive adhesive coating 13 on the inner surface 14 thereof. As can be appreciated from FIGS. 1 through 3, inner surface 14 of conductive element 12 has a substantially flat front, or inner, face. The outer, or rear, surface 15 of conductive element 12 engages the inner, or front, surface 16 of silicone pad 11, while the outer, or rear, surface 17 of silicone pad 11 is in contact with wire loop 18 at one end of electrical lead 19 to establish an electrical connection thereat (lead 19 has insulation 20 surrounding the lead except where the lead is in engagement with silicone pad 11). The other end of lead 19 (from which insulation 20 has been removed) may be connected with an electronic instrument 21 such as an active electronic medical instrument, and this connection may, if desired, be through the use of hook connector 22 as shown in FIG. 4. The active electronic medical instrument may be, for example, a transcutaneous nerve stimulating device such as shown in U.S. Pat. No. 4,014,347.

As best shown in FIG. 3, conductive element 12 may be of a circular configuration (although the shape may be varied as needed or desired), and silicone pad 11 may be of a smaller circular configuration (although again the shape may be varied as needed or desired).

Silicone pad 11, conductive element 12, and conductive adhesive coating 13 are entirely nonmetallic and nonionic. Silicone pad 11 is small in radius relative to conductive element 12 and may be made from a carbon-containing material (and preferably is carbon-filled silicon rubber) so that the conductor is electrically conductive but yet is flexible.

Conductive element 12 is principally a mixture of carbon black and karaya, and is preferably formed from the following:

32 grams carbon black;
125 grams karaya;
720 ml isopropyl alcohol; and
320 ml karaya gum conductive solution.

It has been found that these ingredients may vary by about 20% and yet form an operationally satisfactory conductive element for use in the electrode of this invention.

Conductive element 12 is preferably prepared as follows:

The isopropyl alcohol and karaya are first mixed together with sufficient stirring to achieve thorough mixing, after which the carbon black is added to the solution with the solution again being stirred sufficiently to achieve thorough mixing. The karaya gum conductive solution is then added with stirring of the mixture, again sufficient to achieve thorough mixing. Within about one-half hour, the mixture is poured onto a flat surface to form a solidified sheet of material as it cures. The material is cured for about one day, and may then be cut to size as needed for use as the conductive electrode.

The conductive adhesive coating 13 also includes karaya and is preferably prepared from the following:

15 ml isopropyl alcohol;
10 grams karaya;
8 ml glycerol; and
12 ml karaya gum conductive solution.

It has been found that these ingredients may also be varied by about 20% and yet form an operationally satisfactory conductive adhesive for use in this invention.

The conductive adhesive coating is preferably prepared as follows:

The isopropyl alcohol and karaya are first mixed together with sufficient stirring to achieve thorough mixing. The glycerol is then added, again with sufficient stirring to achieve thorough mixing. The karaya gum conductive solution is then added with stirring, again sufficient to achieve thorough mixing. The resulting mixture is then immediately applied to conductive element 12 since the adhesive will normally congeal in about three to four minutes (a normal maximum set up time is no more than about 15 minutes).

It is essential, in this invention, that the conductive element 12 and conductive adhesive coating 13 provide an air-permeable covering to the skin of a patient so that the skin can "breathe" through the conductive element and adhesive coating. This enables the disposable electrode to be continuously used for relatively long periods of time on the order of a week or longer, whereas other disposable electrodes must be removed in a few days (at least from patients that have skin reactions resulting from contact of the skin with the disposable electrode).

A cover 24 is provided for holding the wire loop 18 in engagement with the back surface 17 of silicone pad 11. Cover 24 is preferably larger than pad 11 and conductive element 12 and has adhesive at the inner side next to pad 11 and conductive element 12. Since cover 24 extends beyond the periphery of conductive element 12, it serves to hold the elements of the electrode in place and also adheres to the skin of a user. Cover 24 is preferably fabric, such as a cotton fabric, for example, and is also air-permeable. As indicated in FIGS. 1 through 3, cover 24 preferably has an ear 25 extending outwardly from the periphery above electrical lead 19.

To position and protect the electrode until use on a patient, a carrier 27, preferably release paper, is utilized. As shown, carrier 27 is releasably in contact with the conductive adhesive coating 13 on conductive element 12 and is also releasably secured to the outer portions of cover 24, which has an adhesive on the inner surface. When so positioned, the outer portions, or edges, of cover 24 surround the front surface 14 of conductive element 12 so that the front surface 13 (with conductive adhesive coating 14 thereon) is effectively sealed between cover 24 and carrier 27.

As also shown in FIGS. 1 through 3, carrier 27 preferably has an ear 28 thereon similar to that of ear 25 on cover 24 so that when carrier 27 is positioned on the electrode, ear 28 extends outwardly from the periphery of the carrier below electrical lead 19 so that ears 25 and 28 form a protective seal extending along the electrical lead.

Electrode 9 may be effectively utilized as a disposable electrode on a patient for a time period of at least a week and such an electrode has been formed, by way of example, to include a conductive element having a front surface of about 1.125 inches diameter with a thickness of about 0.03 inches, a conductive adhesive coating of about 0.020 inches thickness, a silicone pad of about 0.325 inches diameter and a thickness of about 0.020 inches, a cover of about 2.38 inches in diameter and a thickness of about 0.015 inches, and release paper of about 2.5 inches diameter and thickness of about 0.005 inches. It is to be realized, however, that the dimensions and/or shape of the various elements may be modified as needed or desired.

Hook connector 22, as shown in FIG. 4, may be utilized to connect the electrical lead 19 to an electronic medical instrument 21, although other connectors and/or a permanent connection may be made if desired. Hook connector 22, however, provides a quick connection and disconnection that is not readily undesirably disconnected during use (as could occur, for example, by the electrical lead becoming tangled or otherwise effectively shortened to pull the connector from the instrument).

As shown in FIG. 4, hook connector 22 includes an eye portion 30 (which is preferably dipped in an insulating material to form an insulator 31 thereon) having a U-shaped portion 32 extending therefrom with the U-shaped portion having an inwardly-slanted portion 33 near the bottom 34 and an outwardly-directed flange 35 at the end of U-shaped portion 32 adjacent to eye portion 30. A weld 36 is provided at the junction of eye portion 30 and U-shaped portion 32 with the end 37 of electrical lead 19 (from which insulation 20 has been removed) being connected with the hook connector thereat.

Hook connector 22 is simply inserted in a mating female socket (not shown) in the electrical medical instrument 21 so that the hook is maintained therein by frction during use (i.e., the hook is slightly compressed and is therefore slightly spring loaded when in the female socket). When removal is desired, the eye portion is grasped and pulled from the socket.

In another embodiment of the invention (as shown in FIGS. 5 through 8), electrode 39 includes silicone pad 40 having a front, or inner, surface 41 (with a flat front face) and a rear surface 42. In addition, a centrally-positioned, raised flange, or plug, 43 extends longitudinally away from the rear surface 42 of the silicone pad 40 and has an annular shoulder 44 thereon so that a space exists between surface 42 and shoulder 44 to receive wire loop 18 (as shown in FIG. 3) thereon.

Plug 43 is preferably also made from silicon rubber and may be integrally formed with silicon pad 40 with shoulder 44 being of slightly greater radius than the loop of wire loop 18 so that the loop slightly compresses the shoulder during passage over the shoulder to the assembled position (as shown in FIG. 8) wherein loop 18 is held by shoulder 44 in tight engagement with surface 42 of silicone pad 40 and with the lower portion 45 of plug 43 to establish a good electrical contact therebetween. As also indicated in FIG. 8, the top portion 46 of plug 43 may be broken away about shoulder 44 after the wire loop is placed in the assembled position.

A conductive element 48 having a conductive adhesive coating 49 on the inner surface 50 is provided (in the same manner and with the same materials as set forth hereinabove with respect to the embodiment as described in FIGS. 1 through 3) with the outer surface 51 of conductive element 48 engaging the inner surface 41 of silicone pad 40 in the same manner as described hereinabove in connection with the embodiment shown in FIGS. 1 through 3.

A cloth pad, or cover, 53, such as adhesive coated tricot, for example, is provided with the cover being larger in cross-section than both silicone pad 40 and conductive element 48. The inner side of cover 53 has an adhesive thereon to contact the outer surfaces of silicone pad 40 and conductive element 48 with the outer edges extending outwardly thereof. As shown best in FIGS. 5 and 7, cover 53 has a central aperture 54 therein so that plug 43 can extend upwardly therethrough.

A carrier 56 is also provided for protecting the electrode and to hold the elements in place until used on a patient. As shown, carrier 56, which is preferably release paper, is of sufficiently large enough dimensions to cover conductive element 48 (and hence cover conductive coating 49 thereon) and engage the outer edges of cover 53 to effectively form a seal thereat.

Electrode 39 is thus quite similarly structured to electrode 9 except for attachment of the electrical lead to the silicone pad. By way of example, such an electrode can thus have the same dimensions as does electrode 9 except for plug 43 which may have a diameter of about 0.180 inches, a height of about 0.5 inches, and a shoulder of about 0.250 inches diameter. It is again to be understood, however, that the shape and/or dimensions can be modified as needed or desired.

The thus formed electrode is small in size, is flexible, may be utilized without necessity of extensive preparatory steps by the patient or other user, and is air-permeable.

In operation, the electrical lead is connected to the electronic medical instrument (if hook connector 22 is utilized) and/or connected with the silicone pad (if electrode 39 is utilized) for each electrode. The release paper, or other carrier, is then removed from the front face portion of the electrode, and the conductive adhesive is brought into skin contact with the patient at the desired spot (the adhesive on the outer edges of the cover is also brought into skin contact to help maintain the electrode in position). Due to the flexibility and small size of the electrode, the electrode will readily conform to the contours of the skin at the spot selected. In addition, the materials and adhesives utilized are selected to reduce the irritation that might be caused due to the properties of the adhesive, and/or due to lack of skin "breathing" through the electrode, and since the electrode is nonmetallic and nonionic, the danger of incorporation of metals into the body is substantially eliminated.

As can be appreciated from the foregoing, this invention provides an improved, air-permeable, disposable electrode that is well suited for use with an active electronic medical instrument such as a transcutaneous nerve stimulator.

What is claimed is:

1. A skin engageable disposable electrode for use with an electronic instrument having at least one electrical lead connectable with said electrode, said electrode comprising:

a carbon-filled silicone pad having a substantially flat front face portion and a back portion adapted to contact said electrical lead for coupling electrical signals to said electrode; and an air-permeable conductive element including carbon and karaya material and having a substantially flat front face portion with an air-permeable conductive adhesive coating including karaya thereon so that said front face portion is adapted to be engageable with the skin of a user, and a substantially flat back face portion in engagement with said front face portion of said pad, said conductive element being of large size relative to said pad.

2. The electrode of claim 1 wherein said air-permeable conductive element is made from isopropyl alcohol, carbon black, karaya, and karaya gum conductive solution.

3. The electrode of claim 1 wherein said silicone pad includes fastening means, and wherein said electrical lead engageable with said silicone pad has a loop configuration engageable with said fastening means.

4. The electrode of claim 3 wherein said fastening means of said silicone pad engageable with said electrical lead substantially permanently holds said lead in engagement with said silicone pad while said electrode is maintained assembled.

5. The electrode of claim 3 wherein said fastening means of said silicone pad includes a flange over which said loop is received.

6. The electrode of claim 5 wherein said flange includes a shoulder over which said loop passes with said flange above said shoulder being removable after passage of said loop over said shoulder.

7. A skin engageable active electrode for use with an electronic instrument supplying an electrical signal to said electrode through at least one electrical lead connectable with said electrode, said electrode comprising:

first electrically conductive non-metallic conductor means having a first portion of conductive adhesive material adapted to engage the skin of a patient, and a second portion of conductive material having first and second faces with said first portion being at said first face, said first electrically conductive conductor means being air-permeable; and second electrically conductive conductor means of a non-metallic material different from said first electrically conductive conductor means, said second electrically conductive conductor means being in engagement with said second face of said second portion of said first conductor means for establishing electrical contact therebetween, said second electrically conductive conductor means being adapted to be connected with said electrical lead from said electronic instrument.

8. The electrode of claim 7 wherein said second portion of said first electrically conductive conductor means and said second electrically conductive conductor means are carbon-containing and nonionic conductor means.

9. The electrode of claim 8 wherein said first electrically conductive conductor means includes karaya.

10. A disposable electrode for use with an electronic instrument having at least one electrical lead connectable with said electrode, said disposable electrode comprising:

a carbon-filled silicone pad having a substantially flat front face portion and a back portion adapted to contact said electrical lead for coupling electrical signals to said electrode;

an air-permeable conductive element including carbon and karaya material and having a substantially flat front face portion with an air-permeable conductive adhesive coating including karaya thereon so that said front face portion is adapted to be engageable with the skin of a user, and a substantially flat back face portion in engagement with said front face portion of said pad, said conductive element being of large size relative to said pad;

cover means having adhesive on the inner side with the central portion of said inner side engaging said back portions of said pad and said conductive element and having outer portions that extend beyond said conductive element; and carrier means contacting said adhesive coating on said conductive element and said outer portions of said cover means for protecting said electrode until used.

11. The electrode of claim 10 wherein said air-permeable conductive element is made from carbon black, karaya, isopropyl alcohol, and karaya gum conductive solution, and wherein said conductive adhesive coating is made from karaya, glycerol, isopropyl alcohol and karaya gum conductive solution.

12. The electrode of claim 10 wherein said pad has a flange extending rearwardly therefrom, and wherein said cover means has an aperture therein through which said flange extends, said cover means surrounding said conductive element at the outer portions thereof to effect a seal thereat.

13. The electrode of claim 10 wherein said cover means is fabric with adhesive on the side facing said conductive element.

14. The electrode of claim 10 wherein said cover means is adhesive coated tricot.

15. The electrode of claim 10 wherein said carrier means is release paper.

* * * * *